United States Patent [19]

Medabalimi

[11] Patent Number: 6,077,694
[45] Date of Patent: Jun. 20, 2000

[54] METHOD FOR OVER-EXPRESSION AND RAPID PURIFICATION OF BIOSYNTHETIC PROTEINS

[75] Inventor: John Louis Medabalimi, Bethesda, Md.

[73] Assignee: The United States of America as represented by the Department of Health and Human Services, Washington, D.C.

[21] Appl. No.: 07/586,079

[22] Filed: Sep. 21, 1990

[51] Int. Cl.⁷ .............................. C12N 15/62; C12N 15/09
[52] U.S. Cl. .................. 435/69.7; 435/69.1; 435/320.1; 435/219; 435/226; 435/476; 435/488; 536/23.2; 536/23.4; 530/327; 530/324; 530/329
[58] Field of Search .................................. 435/69.1, 69.7, 435/23, 24, 172.3, 320.1, 476, 488, 219, 226; 530/327, 324, 329; 536/23.2, 23.4

[56] References Cited

U.S. PATENT DOCUMENTS

| | | | |
|---|---|---|---|
| 4,987,070 | 1/1991 | Magota et al. | 435/69.7 |
| 5,013,653 | 5/1991 | Huston et al. | 435/69.7 |

FOREIGN PATENT DOCUMENTS

| | | | |
|---|---|---|---|
| 0230869 | 8/1987 | European Pat. Off. | C12N 15/00 |
| 0293249 | 11/1988 | European Pat. Off. | C12N 15/00 |
| 9006369 | 6/1990 | WIPO | C12P 21/00 |

OTHER PUBLICATIONS

Louis, John M., Autoprocessing of the HIV–1 Protease Using Purified Wild–Type and Mutated Fusion Proteins Expressed at High Levels in *Escherichia coli*; Eur. J. Biochem., pp. 199–361–369, 1991.

Bedonelle et al. (1988) Eur. J. Biochem. vol. 171, pp 541–549.

Debouck et al. (1987) PNAS, vol. 84, pp 8903–8906.

S. Scholtissek et al., "A Plasmid Vector System for the Expression of a Triprotein Consisting of β–Galactosidase, a Collagenase Recognition Site and a Foreign Gene Product", Gene 62(1): 55–64, Jan. 1988.

C.V. Maina et al., "An *Escherichia coli* Vector to Express and purify Foreign Proteins by Fusion to and Separation From Maltose–Binding Protein", Gene 74(2): 365–373, Dec. 1988.

D.B. Smith et al., "Single–Step Purification of Polypeptides Expressed in *Escherichia coli* as Fusions with Glutathiona S–Transferase", Gene 67(1): 31–40, Jul. 1988.

P.L. Darke et al., "Human Immunodeficiency Virus Protease: Bacterial Expression and Characterizationof the Purified Aspartic Protease", J. Biol. Chem. 264(4): 2307–2312, Feb. 1989.

*Primary Examiner*—Rebecca E. Prouty
*Attorney, Agent, or Firm*—Morgan & Finnegan, LLP

[57] ABSTRACT

The subject invention relates to a method of producing and purifying large quantities of a biosynthetic protein.

The gene which codes for the protease is placed between the binding domain of a gene which codes for a binding protein and a gene coding for the target protein of interest. The fused gene construct is inserted in an expression vector which is then introduced into a host cell.

3 Claims, 6 Drawing Sheets

5' oligonucleotides:

Fragments 1:
```
(Kpn1 site)                 Ile Glu Gly Arg Pro (Ddel site)
    CC GGC CGG GGA TCC ATC GAG GGT AGG CC
CAT GGG CCG GCC CCT AGG TAG CTC CCA TCC GGAGT
```

Fragments 2:
```
(Kpn1 site)                 Ile Glu Gly Arg Gly
    CC GGC CGG GGA TCC ATC GAG GGT AGG gga gcc gat
CAT GGG CCG GCC CCT AGG TAG CTC CCA TCC cct cgg cta
                                        Phe Pro
aga caa gga act gta tcc ttt aac ttc CC
tct gtt cct tga cat agg aaa ttg aag GGAGT
```

3' oligonucleotides:

Fragments 3:
```
(Ddel site)                         Phe TER (Xba1 site)
T CAG ATT GGT TGC ACT TTA AAT TTT TAA T
  C TAA CCA ACG TGA AAT TTA AAA ATT AGATC
```

Fragments 4:
```
(Ddel site)                         Phe Pro
T CAG ATT GGT TGC ACT TTA AAT TTT ccc att agt cct
  C TAA CCA ACG TGA AAT TTA AAA ggg taa tca gga att gaa act gta cca gta aaa tta aag cca gga atg gat
taa ctt tga cat ggt cat ttt aat ttc ggt cct tac cta
            TER (Xba1 site)
ggc cca TAA T
ccg ggt ATT AGATC
```

FIG. 2A

METHOD FOR OVER-EXPRESSION AND RAPID PURIFICATION OF BIOSYNTHETIC PROTEINS

BACKGROUND OF THE INVENTION

1. Technical Field

The subject invention relates to a method of producing and purifying large quantities of biosynthetic proteins.

The gene which codes for a retroviral protease is placed between the binding domain of a gene which codes for a binding protein and a gene coding for the target protein of interest. The fused gene construct is inserted in an expression vector which is then introduced into a host cell.

2. Background Information

Gene fusions have been used successfully to express and purify proteins produced from recombinant DNA molecules. A common class of fusions involves β-galactosidase whereby the fusion protein is expressed in *E. coli* using the ribosome binding site and the translational start of lacZ (Shuman et al., *J. Biol. Chem.* 255:168–74 (1980) and Silhavy et al., "Experiments With Gene Fusions," (Cold Spring Harbor Laboratory 1984)). Such hybrid proteins can be purified by affinity chromatography using anti-β-galactosidase affinity columns. A similar fusion system uses protein A from *Staphylococcus aureus* (Löwenadler et al., *EMBO* 5:2393–98 (1986) and Valerie et al., *Gene* 58:99–107 (1987)) or a synthetic IgG-binding domain of protein A to purify fusion proteins by binding to an IgG resin (Löwenadler et al., *Gene* 58:87–97 (1987)).

The most widely used enzyme for isolating the target protein from the fusion protein involves a protease cleavage site specific to factor Xa protease. Employing the factor Xa protease recognition site to release the target protein, in the present studies, was not successful even by providing an Arg-Gly bond. The entire factor Xa gene has never, in the past, been inserted between the binding protein and the target protein.

Most serine proteases either fail to cleave Arg-Pro bonds or do so very slowly. Factor Xa has a strong preference for Arg-Gly bonds in addition to its specificity for the Ile-Glu-Gly-Arg sequence. The cleavage is dependent on the nature of target protein and the conformation of the fusion protein, in addition to several other factors.

A protease of recent interest is the one produced by the human immunodeficiency virus. This virus is the causative agent of the acquired immunodeficiency syndrome (AIDS) (Barre-Sinoussi et al., *Science* 220:868–70 (1983) and Gallo et al., *Science* 224:500–502 (1984)). The genome size mRNA, like that of other retroviruses, has a gag-pol-env organization and is translated into the Pr55gag and Pr160gag pol polyproteins. HIV-1 like all other replication competent retroviruses, encodes a protease (PR) which is responsible for the specific cleavage of Pr55gag and Pr160gag pol into the mature gag derived structural proteins p17, p24, p7 and p6, and the pol derived protease (PR), reverse transcriptase (RT) and the endonuclease, the integration protein (IN). Protease deficient mutants of the murine leukemia virus and of HIV were shown to produce immature noninfectious virus particles (see Meek et al., *Nature* 343:90–92 (1990) and McQuade et al., *Science* 247:454–56 (1990)). These studies suggested that the protease may be a potential target for drug therapy (see also Moore et al., *Biochemical and Biophysical Research Communications* 159:420–25 (1989)). The requirements for sufficient quantities of enzyme for structural and biochemical studies necessitated expression of the protease in *E. coli* and yeast. (Kraussich et al., In *Annual Review of Biochemistry* (Richardson et al., eds.) Vol. 55, pp. 701–54 (1984) and Oroszlan et al., In *Current Topics in Microbiology and Immunology* (Swanstrom et al., eds. (1990)). Structural analysis of the active human immunodeficiency virus-1 (HIV-1) protease has shown that it is a homodimer possessing one active site. The active site of the protease contains two sequences of AspThrGly, common with the other known aspartic proteases (Wlodawer et al., *Science* 245:616–21 (1989) and Lapatto et al., *Nature* 342:299–302 (1989)). Recently, it was demonstrated that inhibitors of the HIV-1 protease arrest the maturation of HIV-1-like particles (Heek et al., *Nature* 343:90–92 (1990) and McQuade et al., *Science* 247:454–56 (1990)). Expression of the protease gene (297 bp) in *E. coli* provided low recovery of the pure protease (McKeever et al., *J. Bio. Chem.* 264:1919–21 (1989)). The protease gene expressed as a fusion with flanking truncated gag-pol region sequences resulted in the self-processing of the protease in *E. coli* (Debouk et al., *Proc. Natl. Acad. Sci. USA* 84:8903–06 (1987)).

Furthermore, a study was done on the expression of the HIV-1 protease as a fusion with the LacZ of *E. coli* (Giam et al., *J. Biol. Chem.* 263:14617–20 (1988)). In this case, the expressed fusion was partially soluble, and the majority of the product was found in the inclusion bodies. Consequently, a single column purification of the fusion product, immediately after lysis of the cells, cannot be performed since the fusion protein is insoluble. Purification of the fusion protein from the inclusion bodies involves considerable loss in the final amount of the protease recovered.

In another system, the target protein was fused to the maltose binding protein (MBP) coded for by the malE gene of *E. coli* (Amann et al., *Gene* 67:21–30 (1985) and Maina et al., *Gene* 74:365–73 (1988)).

This latter approach uses a crosslinked amylose resin as an affinity matrix to purify the MBP fusion protein. A high yield of pure fusion protein is obtained using a single purification step carried out under non-denaturing conditions. This system of expression would allow for the separation of the target domain from the MBP domain by the site-specific proteolytic cleavage (factor Xa, specific cleavage at the tetrapeptide, IleGluGlyArg) after purification. Thus, if the recognition site is placed before the target protein domain, factor Xa will cleave specifically at the site releasing the target protein without any additional N-terminal residues.

Unfortunately, there are many disadvantages to this procedure. For example, as the present inventors observed, utilizing clone A, the target protein does not undergo cleavage using the factor 10a protease.

Furthermore, there are many advantages to the use of the HIV-1 protease of the present invention rather than the factor Xa protease. Although literature exists which shows that the factor Xa protease can cleave, in some cases, fusion proteins after denaturation, it has never been incorporated as one of the components in the fusion protein, like the HIV-1 protease. The HIV-1 protease, as one of the components of the fusion protein of the present invention, has been shown to renature and cleave itself completely from the fusion protein. Furthermore, the HIV-1 protease, being a smaller enzyme than the factor Xa protease, would be expected to more readily effect cleavage at the appropriate cleavage site in the fusion protein and thereby more efficiently release the target protein from the fusion protein.

SUMMARY OF THE INVENTION

The subject invention relates to a method of producing and purifying large quantities of biosynthetic proteins.

The gene which codes for the protease is placed between the binding domain of a gene which codes for a binding protein and a gene coding for the target protein of interest. The fused gene construct is inserted in an expression vector which is then introduced into a host cell.

More specifically, the present invention relates to a method of producing a protein comprising the steps of:

i) constructing an expression vector comprising
  (a) a sequence encoding a binding domain;
  (b) a sequence encoding a protease which is downstream of said sequence (a) and is flanked by an amino acid sequence which is specifically recognized said protease;
  (c) a sequence encoding a target protein which is downstream of sequence (b) wherein said sequences (a), (b) and (c) are downstream of and operably linked to a promoter;

(ii) inserting said vector into a host cell; and (iii) culturing said cell under conditions such that said sequences (a), (b) and (c) are expressed and the fusion product encoded therein produced.

The method may further comprise the step of effecting proteolytic cleavage by the protease at the flanking sequences. The protease itself may be that produced by a retrovirus (i.e., a retroviral protease).

The present invention also includes a method of producing a protein comprising the steps of:

(i) constructing an expression vector comprising
  (a) a sequence encoding a binding domain;
  (b) a sequence encoding a protease cleavage site which is downstream of said sequence (a);
  (c) a sequence which is encoded by a target protein which is downstream of sequence (b) wherein said sequences (a), (b) and (c) are downstream of and operably linked to a promotor;

(ii) inserting said vector into a host cell; and (iii) culturing said cell under conditions such that said sequences (a), (b) and (c) are expressed and the fusion product encoded therein is produced.

The sequence of step (b) may encode a retroviral protease cleavage site. Furthermore, this latter method may further comprise the step of effecting proteolytic cleavage by digesting the fusion product with pure protease supplied in catalytic amounts.

In both of the methods referred to above, the binding domain may be selected from the B-galactosidase binding domain, the Protein-A domain, the IgG-binding domain, the maltose-binding domain and the glutathione-S-transferase binding domain.

The methods described above may also be used to produce large quantities of proteases, particularly retroviral proteases.

All patents and publications referred to herein are hereby incorporated by reference.

B shows the pCG807fx map and the sites chosen for cloning. Clone A contains the exact coding region of 297 bp placed immediately adjacent to the Arg (factor 10 cleavage site). Clone B contains a portion of the pol region flanking both ends of the protease gene. Upon synthesis, the size of the full-length clone B product should correspond to a molecular mass of 52 kDa and clone A to 49 kDa.

Figure 3:
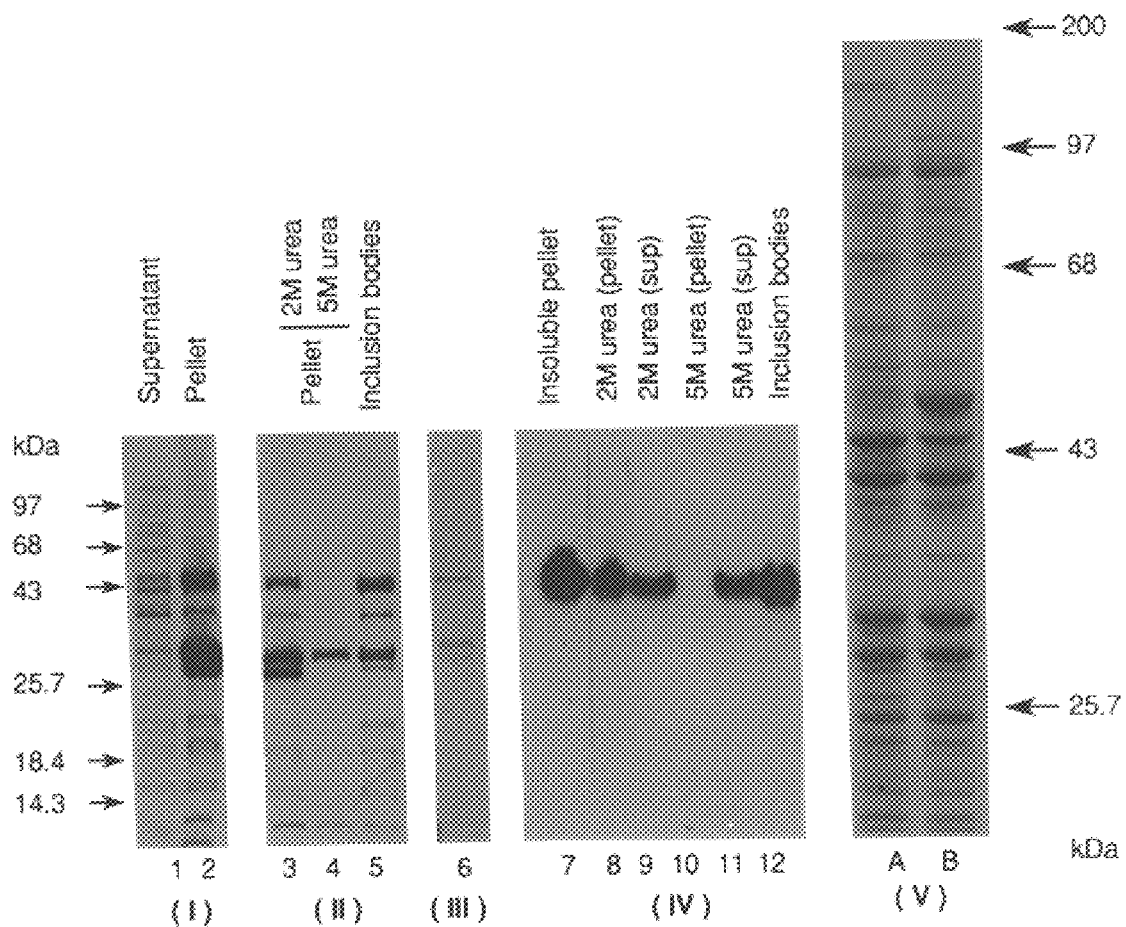

FIG. 3 represents the expression and partial purification of the full-length fusion from clone A. In panels (I) to (III) and (V) proteins were staining using Coomasie Blue. Panel (V) shows 10% SDS-PAG analysis of crude lysates (25 μg protein) prepared from uninduced (A) and induced (B) cells. In panels (I) to (IV), electrophoresis of proteins was utilizing 10–20% gradient SDS-PAGE. Panel (I) shows analysis of 7.5 μg protein from the soluble supernatant (lane 1) and insoluble pellet (lane 2), after sonication of the cells in buffer A. The insoluble pellet derived after treatment of the inclusion bodies (lane 5) using 2 M and 5 M urea are shown in lane 3 and 4 respectively. An immunoblot is shown in panel (IV). Lane 7 shows the insoluble pellet (1.5 μg). Equal amounts of protein (2 μg) from the supernatant and pellet obtained after 2 M urea solubilization are shown in lane 8 and 9. The pellet obtained after 2 M urea treatment was supernatant that were analyzed are shown in lanes 10 and 11. Lane 12 shows 1 μg of inclusion bodies. Lane 6 shows 1 μg of the inclusion bodies prepared from clone A, solubilized in 5 M urea and subsequently dialyzed against decreasing concentrations of urea to a final buffer containing 25 mM sodium phosphate (pH 6.5), 1 mM DTT, 1 MM EDTA, 5% glycerol. This preparation showed a significant enrichment of the fusion protein (ca 50% of total protein) which was assayed for specific proteolytic activity using the synthetic peptide substrate (Louis et al., *Biochem. Bioghvs. Res. Comm.* 164:30–38 (1989) and Louis et al., *Biochem. Biophys. Res. Comm.* 159:87–94 (1989)).

Figure 4:
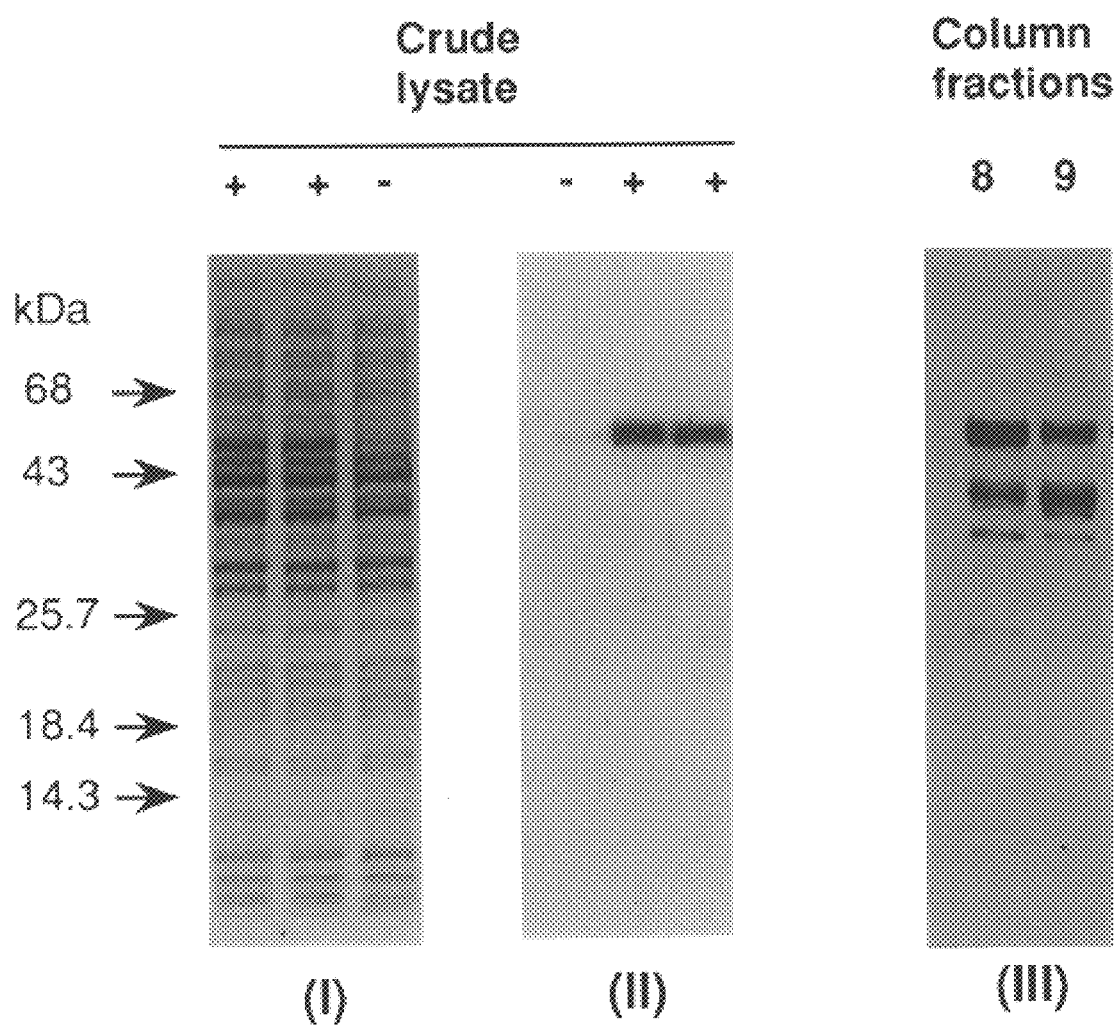

FIG. 4 represents the expression and purification of the full-length fusion protein from clone B. Soluble lysate (10 μg) prepared from 2 identical clones, induced (+) nd uninduced (−) are shown in panel (I). Panel (II) shows the same samples (2 μg) immunoblotted. Panel (III) shows the two peak fractions of the purified fusion protein (1.5 μg) after amylose column chromatography. Analysis of samples was on 10–20% gradient SDS-PAG. Proteins were stained using Coomasie Blude in panels (I) an (III).

Figure 5:
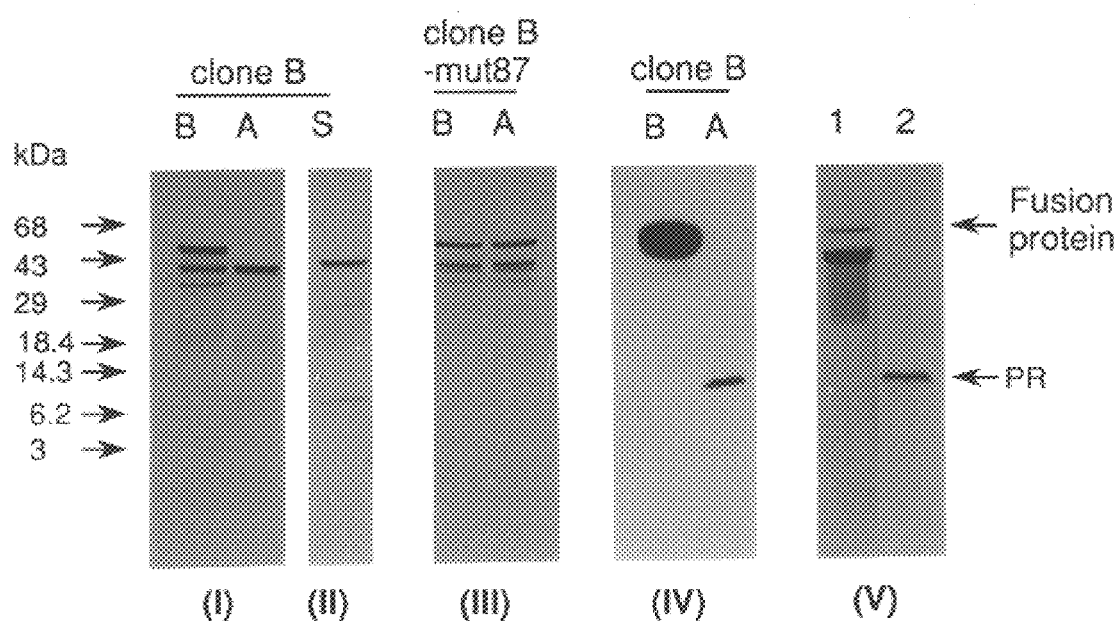

FIG. 5 represents the in vitro processing from the fusion protein and purification of the protease 2 μg of purified fusion protein before (B) and after (A) the refolding steps was analyzed on 10–20% gradient tricine polyacrylamide gels. In panels (I), (III) and (V) proteins were visualized by Coomasie staining and in panel (IV) by immunoblotting. Panel (II) shows the same preparation as in panel (I), lane A by silver staining. Panel (V), lane 12 shows the major band of the maltose binding protein (38 kDa) and lane 2,400 ng of the purified protease. Positions of molecular weight markers in kDa are shown on the left. The positions of the migration of the full-length fusion protein (53 kDa) and that of the protease (11 kDa are indicated by arrows.

Figure 6:
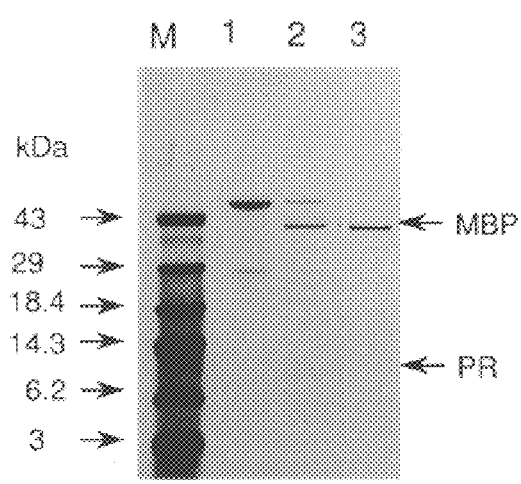

FIG. 6 represents in vitro processing of the mutant protease from the fusion protein using the wild-type protease.

Lane 1 shows 600 ng of the full-length fusion protein expressed and purified from clone B-Mut87. Lane 2 shows the same amount of fusion protein incubated with 12 ng of the purified wild-type protease at 37° C. for 1 hr in a buffer containing 150 mM NaCl, 50 mM sodium phosphate, pH 6.5, 1 mM DTT. Lane 3 shows 0.5 μg of purified maltose binding protein. All samples were electrophoresed on 10–20% tricine polyacrylamide gels and stained with Coomasie blue. Purified protease (12 ng) was undetectable by Coomassie staining. The positions of the MBP and the PR are indicative by arrows on the left. Molecular weight standards are shown in lane M.

DETAILED DESCRIPTION OF THE INVENTION

The subject invention relates to a method of producing and purifying large quantities of a biosynthetic protein. The three basic components which are necessary in order to carry out the method of the present invention include: 1) a binding protein, 2) a target protein and 3) a retroviral protease.

The binding protein utilized may be any protein which contains a binding domain. The binding domain consists of sequences providing confirmation to bind to specific matrices. The purpose of the binding protein is to allow purification of the protein in a single column step under denaturing or nondenaturing conditions.

The target protein produced by the method is any biosynthetic protein that is resistant to the proteolytic action of the protease and capable of renaturing in vitro.

Figure 1:
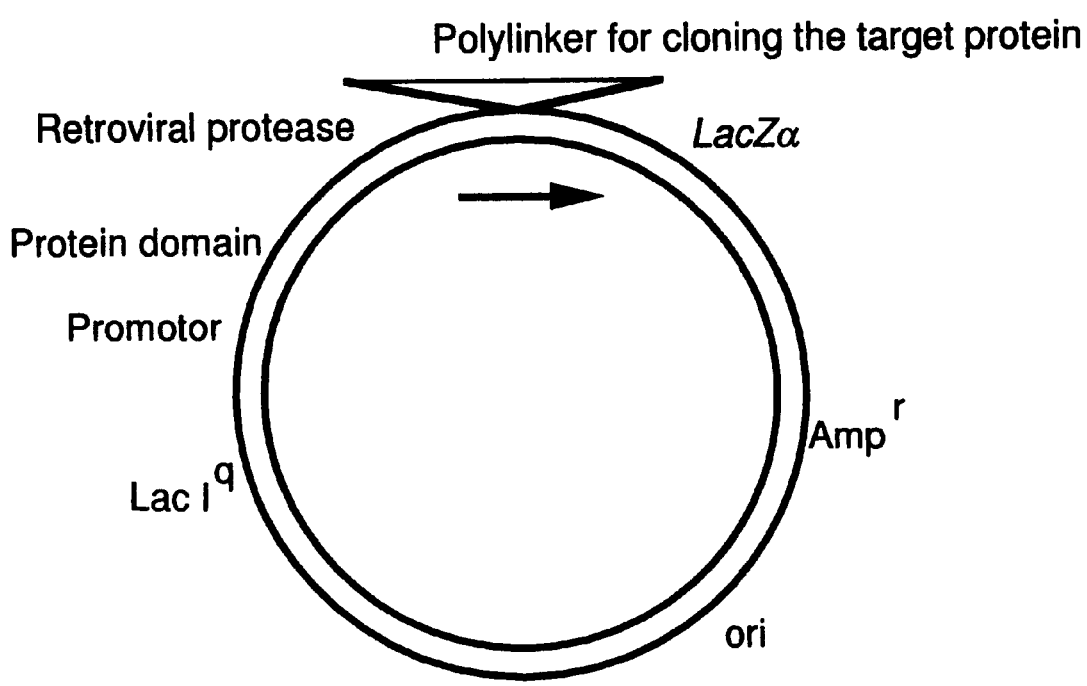
FIG. 1 represents the backbone structure of a suitable expression vector.

The protease used in the method, advantageously a retroviral protease, may be any protease which is capable of autoprocessing while the fusion protein is undergoing renaturation in vitro. One example of a suitable protease is HIV-1 protease. The entire gene which encodes the protease can be placed between the gene encoding the binding protein and the gene encoding the target protein (FIG. 1). Where the entire protease gene is utilized, it is advantageously flanked on each side by at least 4 amino acids of the pol gene, which are in the same reading frame as that of the protease gene.

A retroviral protease cleavage site sequence may be inserted, in lieu of the complete protease gene, between the binding protein and the target protein. Where this technique is used, exogenously supplied protease can be supplied to the soluble fusion protein in order to cleave the fusion protein into its various components, thereby releasing the target protein of interest.

The precise features and steps comprising the method of the present invention are specified below.

Initially, it should be noted that any expression vector can be used. The vector utilized determines the copy number. For example, a pBR322 fragment can be used which spans the nucleotide sequence from AvaII to EcoRI. Furthermore, the vector can be any other that is commercially available for expression of proteins (e.g. PKKK-233-2 (Pharmacia Biotechnology), PKKK-233-2, HIV-1 and Rous Sarcoma Virus (RSV)) which can be modified so as to contain the retroviral protease gene (e.g. HIV-1, RSV, etc.).

The lac or tac promotor, commonly used for inducing the expression of unfused or fused gene products, can be inserted into the vector. Alternatively, the T7 promotor can be used.

A sequence encoding the binding domain is cloned downstream of and in operable linkage with the promotor. This sequence contains the translational start codon ATG. Suitable binding domains permit purification to be effected in a single column step. Suitable binding domains include, for example, β-galactosidase domain, Protein-A domain, IgG-binding domain, the maltose-binding domain, and the glutathione-S-transferase domain.

A sequence encoding the protease is inserted downstream of the binding domain. This sequence can be flanked by a further sequence coding for at least 4 amino acids of the pol gene. The HIV-1 protease gene (uppercase) containing the flanking region sequences (lowercase) is shown below:

```
5'ggagccgatagacaaggaacttatcctttaacttcCCTCAGATCACTC

TTTGGCAACGACCCCTCGTCACAATAAAGATAGGGGGCAACTAAAGGAA

GCTCTATTAGATACAGGAGGAGATGATACAGATATTAGAAGAAATGAGTT

TGCCAGGAAGATGGAAACCAAAAATGATAGGGGGAATTGGAGGTTTTATC

AAAGTAAGACAGTATGATCAGATACTCATAGAAATCTGTGGACATAAAGC

TATAGGTACAGTATTAGTAGGACCTACACCTGCAACATAATTGGAAGAAA

TCTGTTGACTCAGATTGGTTGCACTTTAAATTTcccattagtcctattga aactgtaccagtaaaattaaagccaggaatggatggccca3'
```

A minimum of 7–8 amino acids can be necessary for the retroviral protease, used in the fusion construct, to recognize the cleavage site. Moreover, the amino acids present in the cleavage site are specific to the protease being utilized for cleavage. Approximately 4 of these amino acids are inherent to the protease gene (provided the entire protease gene is inserted), and approximately 4 other amino acids are added which flank the gene.

In an alternative approach, the sequence coding for at least a heptapeptide, corresponding to any of the cleavage sites recognized by the protease, can be inserted between the binding domain encoding and the target protein encoding sequences. In this inserted sequence, approximately 3–4 of the amino acids are inherent to or part of the protease gene, as discussed above, whereas the other approximately 3–4 amino acids are the "added" or flanking amino acids, also discussed above.

Multiple restriction sites for the insertion of the target gene can be present downstream of the binding domain. It is preferable to maintain the number of sites in the multiple cloning region (MCR) to a minimum. A nucleotide sequence coding for a translation termination codon, in all 3 reading frames, can be inserted downstream of the target protein encoding sequence.

A sequence encoding the target protein of interest can be inserted in the multiple cloning site in the appropriate reading frame. The resulting construct can be introduced into an appropriate host cell. The transformed cells, after lysis, and fractionation into the soluble and the insoluble fractions, can be analyzed to determine the solubility of the protein.

When the fusion protein is produced in an insoluble form, it is present in the form of inclusion bodies. The insoluble pellet which contains the inclusion bodies is washed in a buffer containing sodium phosphate, DPT, and Triton X-100. The protein is thereby removed, and the inclusion bodies are left in the pellet.

If the fusion protein is present in the soluble fraction (aggregated or non-aggregated form), then the full-length protein can be purified using affinity column chromatography, depending on the type of binding domain fused to the target protein.

The fusion protein, either isolated from the inclusion bodies or purified by affinity column chromatography, is solubilized in urea and subsequently renatured. The protease in the fusion protein is capable of forming an active dimer under these conditions and cleaving itself from the fusion protein. In this process, the target protein is released. The solution containing the mixture of the three proteins can be either purified on the same affinity column that was used previously or by any other method (for example, size-exclusion or ion-exchange chromatography).

When the protease cleavage site is provided, instead of the protease gene, the fusion protein that is purified either from the inclusion bodies (insoluble) or by affinity column purification (soluble) is digested using purified protease to release the target protein.

Thus, the ultimate purpose of the protease is to cleave the domain between the target protein and the protease in the fusion product. The protease also cleaves the binding protein from the protease. Consequently, the fusion product is cleaved into separate units or components. Thus, large quantities of both biosynthetic proteins and proteases, particularly retroviral proteases, can be produced due to the cleavage of the fusion protein.

Furthermore, in the present invention, by adding pol region sequences (i.e., twelve amino acids at the N-terminal region of the protease and nineteen amino acids at the C-terminus) flanking the protease (clone B), the fusion protein is produced as a soluble protein in E. coli. In contrast, a product which does not contain the Pol region sequences is produced as an insoluble protein (see product of clone A).

Thus, in view of the above, the present invention is a simple and rapid method (2 to 3 days) for the purification of target proteins, as well as proteases, both in high yield (FIG. 1). This approach offers a convenient method whereby polyproteins of various lengths containing the protease and the gag or the pol domains can be obtained in sufficient quantity and purity for studies on the mechanism of protease activation and subsequent proteolysis of the polyprotein in vitro. The various cleavage products can be isolated easily, and intermediate products of the polyprotein can be identified thereby allowing the determination of the order of cleavage. The effect of mutations at the various cleavage sites can also be studied.

The above-described method, using a retroviral protease, manifests a new approach for designing constructs useful for expression and efficient purification of proteins. An expression vector can be constructed containing the coding sequence of the protease gene (e.g., HIV-1 or other retroviral proteases) together with a minimum of 4–5 amino acids flanking the protease to provide the specific recognition sequences for cleavage by the protease, inserted between the binding domain (for example, the maltose protein binding domain) and the target protein. A minimum of 7 amino acids of the substrate spanning the cleavage site is required for HIV-1 protease specific cleavage (Darke et al., *Biochem. Biophys. Res. Comm.* 156:297–303 (1988)). The fusion protein either isolated from the inclusion bodies (insoluble) or by affinity column chromatography (soluble) can be treated with urea followed by renaturation. The self-processing by the protease will then release the target protein. However, this approach will be useful only if this alteration (4–5 additional N-terminal residues) does not affect the biological activity of the target protein. Alternatively, in some cases, the natural N-terminal sequence of the target protein may serve as the P' side (i.e., the amino acid residue which counters specificity) of the newly created cleavage site. In all cases, this strategy can be applied only if the binding domain and the target protein are resistant to the proteolytic action of the protease. Otherwise, this method would cleave the target protein, and only a truncated protein product would be obtained.

By mutating either one of the cleavage sites at the N- or the C-terminal region of the protease, it is still possible to accomplish cleavage at the non-mutated site. A construct containing only the pol region sequences between the protease and the target protein can be advantageous since the cleavage of such a fusion protein results in two proteins (i.e., the binding domain together with the protease, and the target). Repassing such a mixture on the same affinity column allows for purification of the target protein in two column steps.

An alternative possibility would be to insert, between the binding domain and the target protein, a protease cleavage site and accomplish the cleavage by pure protease supplied extraneously in catalytic amounts. The fusion protein from clone B-mut87 was cleaved using the wild-type protease to release the mutated protease (See FIG. 5).

Furthermore, the procedure used for renaturing the protease, of the present invention, can be applied as a general method to renature proteins which are present in the form of soluble aggregates, or inclusion bodies, to obtain them in their active form.

When the fusion protein is produced as an insoluble protein in E. coli, the fusion protein, which can be isolated in the form of inclusion bodies, can be solubilized, cleaved in vitro, and passed through the affinity column to purify the target.

In view of the above discussion, it is apparent that the present method can be used for the over-expression of proteins in either eucaryotic or procaryotic cells, as well as for the purification of these proteins. Basically, a retroviral protease or a retroviral protease cleavage site is used to separate the target protein from the full-length fusion protein.

The present invention can be illustrated by the use of the following non-limiting examples.

EXAMPLE 1

Cloning the Protease Gene Fused to the Maltose-Binding Protein Domain and the Target Protein Domain The vector pCG807fX was utilized for over-expression. This vector contains the PBR322 (Ara 1 to EcoR1) backbone (Amann et al., *Gene* 40:183–90 (1985)) and a Lac promoter cloned upstream from the malE gene which is fused in frame with the LacZ gene (Guan et al., *Gene* 67:27–30 (1988) and Maina et al., *Gene* 74:365–73 (1988)).

Figure 2B:
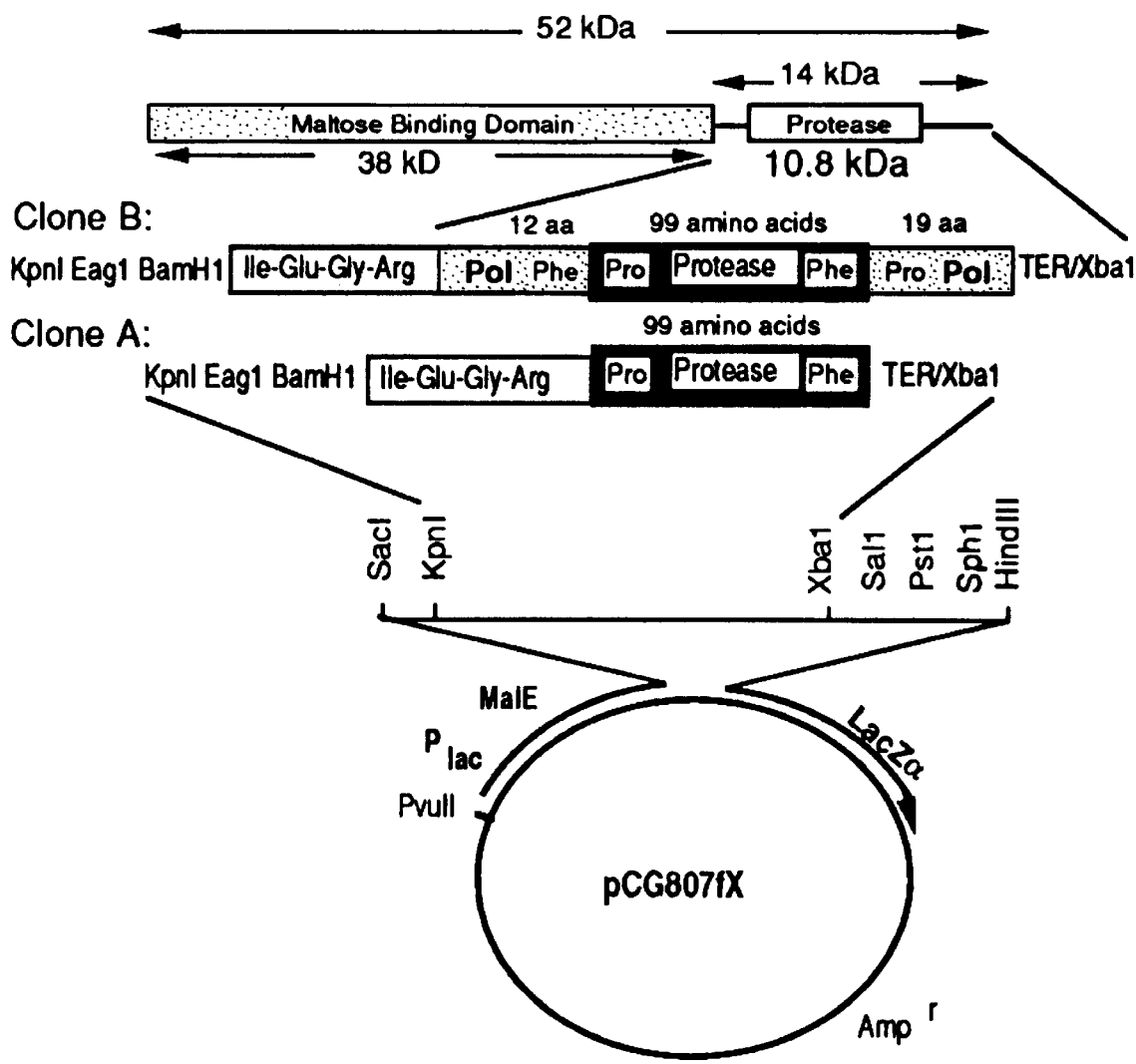
FIG. 2 represents a strategy for the construction of the expression vector containing the HIV-1 protease fused to the maltose-binding protein domain. In A, the various oligonucleotide fragments that were synthesized are shown. These fragments contain the cohesive ends compatible to the cloning sites. The uppercase sequence denotes a portion of the polylinker sequence and the bolded uppercase, the sequence necessary for factor 10 recognition. The uppercase underlined sequence represents the remaining protease coding region (nucleotide positions 1 to 2 and 273 to 297) added to the 270 bp Ddel fragment. The lowercase sequence corresponds to 12 amino acids and 19 amino acids of the pol gene sequence added at the amino terminus and the carboxyl terminus of the protease, respectively.

The malE vector, pCG807fX was digested with restriction endonuclease, Kpn1 and Xba1. The linearized plasmid that was purified contains the entire sequence of the vector, minus the sequence placed between the Kpn1 and Xba1 sites of the polylinker containing the site necessary for the factor 10a protease recognition (FIG. 2B). The Ddel fragment contains 270 bp of the protease coding region of 297 bp from nucleotide position 3 through 272. In order to isolate this 270 bp Ddel fragment, the HIV-1 clone BH5 (Ratner et al., *Nature* 313:277–84 (1985)) was digested with Bgl2 and Bali to obtain a 561 bp fragment which was subsequently digested with Dde1. The purification of the DNA fragments was by preparative agarose (SeaKem NuSieve GTG or GTG agarose, FMC, ME) gel electrophoresis. Oligonucleotides for the coding and non-coding strands were synthesized. As shown in FIG. 2A, complementary oligonucleotides were annealed and fragments 1 and 3 were mixed with the 270 bp Dde1 fragment (wild-type) and the linearized pCG807fX for ligation to obtain clone A. Clone B was obtained by replacing fragments 1 and 3 with fragments 2 and 4. The recombinant mutant construct (Louis et al., *Biochem. Biophys. Res. Comm.* 164:30–38 (1989)) was digested with EcoR1 and Hind3 to obtain a 579 bp DNA fragment which spans the protease gene. This 579 bp fragment was further digested with Ssp1 and Dde1 to isolate the 270 bp Ddel fragment. Clone B-mut87 was obtained by replacing in ligation with the wild-type 270 bp fragment, the mutant 270 bp fragment. All reactions were four piece directional ligations. All plasmid constructs were used for transformation of competent JM109 cells. Six recombinants from each ligation were used for restriction endonuclease analysis and 2 positive clones containing the correct size insert were used for sequencing (Maniatis et al., *Molecular Cloning: A Laboratory Manual* (1982)).

EXAMPLE 2

General Protocol for Expression and Purification of the Wild-Type and Mutant Fusion Proteins For large scale preparation of the fusion protein, *E. coli* bearing the appropriate plasmid construct were grown at 37° C. to 0.5 O.D. (A 600 nm) in 200 ml Luria-Bertani broth (LB) containing 0.1% glucose and induced with 1 mM isopropyl-β-D-thiogalactosidase for 90 min. Small scale cultures were grown as mentioned above in 3–5 ml LB. Cells were harvested by centrifugation at 3600×g for 15 min, 4° C. The cell pellet (200 ml culture) was washed in 35 ml of phosphate buffered saline (Gibco-BRL,MD) and suspended in 16 ml of "buffer A" (50 mM Tris-HC1 (pH 6.5), 30 mM MaCl1 mM EDTA, 1 mM DTT, 0.5% NP-40, and 1 mM phenylmethysulphonyl fluoride (see Louis et al., *Biochem. Biophys. Res. Comm.* 159:87–94 (1989)). The cell suspension was lysed by sonication and the lysate centrifuged at 9500×g for 30 min, 4° C. to obtain the soluble fraction. Cross-linked amylose resin (20 ml) was washed thrice in 30 ml of column loading buffer (10 mM sodium phosphate (pH 6.5), 30 mM NaCl, 0.25% Tween-20, 1 mM DTT), packed in a FPLC XK 26/20 (2.6×18 cm) chromatography column (Pharmacia-LKB Biotechnology), and equilibrated with three to five column volumes of the same buffer. The soluble supernatant (125 to 150 mg protein) was passed through the column at a flow rate of 1 ml/min at 4° C. The column was washed with five column volumes of buffer containing 10 mM sodium phosphate (pH 6.5), 0.5 M NaCl, 1 mM DTT and 1 mM DDt and 1 mM EDTA. The bound fusion protein was eluted with 10 mM sodium phosphate (pH 6.5), 0.5 M NaCl, 10 mM maltose, 1 mM EDTA and 1 mM DTT. Fractions (15×2 ml) were collected, estimated for protein content and the peak fractions were pooled (Guan et al., *Gene* 67:21–30 (1988) and Maina et al., *Gene* 74:248–54 (1976)).

EXAMPLE 3

Rapid Purification and In Vitro Processing of the Full Length Wild-Type Fusion Protein of Clone B Cell lysate derived from 200 ml of culture (clone B) was passed through cross-linked amylose column, and the resin was washed until all the unbound protein was removed. Bound fusion protein was eluted in a buffer containing 10 mM maltose. The peak fractions when analyzed showed the presence of the full-length fusion product (53 kDa) in addition to the truncated protein and other trace contaminants; the major truncated product (38 kDa) was the maltose-binding domain (FIG. 3, lanes 8 and 9). By pooling the peak column fractions, it was estimated that 40–52.5% of the total protein that was purified was the full-length fusion protein. Anti-maltose binding protein serum showed reactivity to the same 53 kDa protein in addition to the truncated maltose binding protein domain (38 kDa). The full-length protease fusion protein eluted as multimer, as evidenced by size exclusion chromatography (data not shown). The aggregation could have occurred in *E. coli* or during the purification on the amylose column since a high protein concentration of ac. 1 mg/ml protein was observed at the peak maximum. The loss of self-processing of the fusion protein could be due to this aggregation or due to improper folding of the protease. This proved to be advantageous because it allowed a single column purification of the fusion protein and also for studies on the activation and self-processing of the protease from the fusion protein in vitro.

For in vitro processing of the protease from the fusion protein, the combined peak fraction from the amylose column was diluted to a concentration of 100 μg/ml protein in a final buffer of 5 M urea, 10 mM DTT, 50 mM Tris-HCl (pH 6.5), 1 mM EDTA, 0.5% NP-40. This solution was dialyzed against decreasing concentrations of 4, 2, 1, 0.5, 0.25 M urea in a buffer of 50 mM sodium phosphate (pH 6.5), 1 mM DTT, 1 mM DDT, 1 mM EDTA, 30 mM NaCl for a period of 45–60 min each. The final dialysis buffer contained 25 mM sodium phosphate (pH 6.5), 1 MM DTT, 1 mM EDTA, 5% glycerol. Under these conditions the protease showed complete cleavage from the wild-type full-length fusion protein. FIG. 5 shows the products analyzed before (B) and after (A) this "refolding" procedure. In panel I, lane B, the full-length product migrated at a position corresponding to a size of 53 kDa as mentioned before. After the refolding procedure, the full-length product was reduced in size to products migrating at the position of the maltose binding protein domain (30 kDa) and showed the appearance of a 11 kDa product barely visible by Coomasie staining (panel I lane A). Lane S shows the refolded preparation of silver staining which shows the distinct presence of the 11 kDa band. Panel IV (lanes B and A) shows the immunoblotting analysis of the same preparation and confirmed that the 11 kDa band was the protease processed from the fusion protein. Complete cleavage of the protease was observed in cases when varying concentrations of the fusion protein (5 μg up to 250 μg/ml) was used in the refolding method.

EXAMPLE 4

Purification of the 11 kDa Protease

After the refolding procedure, the protein preparation which contains a major proportion of the maltose-binding protein domain, and the protease was dialyzed against 100 fold excess buffer containing 50 mM MES (pH 6.5), 1 MM EDTA, 1 mM DTT and 5% glycerol for 3–4 hr. at 4° C. The proteins were separated on a cation exchange column (Mono S) using a gradient program of 0 to 0.225 M Nacl in 15 min at a flow rate of 1 ml/min at room temperature. Approximately 35% of total protease activity eluted at 0.1 to 0.15 M sodium chloride to provide protease which was ≧95% pure (FIG. 4, panel (V), lane 1). The maltose binding protein domain did not bind to the resin and was collected in the void volume. A higher recovery of enzyme activity (~90%) was obtained by repassing the refolded protein solution through the amylose column. The major proportion of the maltose binding protein domain bound to the column (FIG. 5, panel (V), lane 2), and the protease in the void volume was about 50% pure.

Starting with 170 mg of crude lysate prepared from 200 ml culture of clone B (induced aT 0.4 to 0.5 absorbance at 600 nm), 5.6 mg of fusion protein was obtained upon amylose column purification. After the refolding procedure, 4.2 mg of protein gave a recovery of ≧180 µg of protease following the cation exchange column purification.

EXAMPLE 5

In Vitro Processing of a Fusion Protein Containing the Mutated Protease by Extraneous Wild-Type Protease Clone B-mut87 was expressed, purified by amylose column chromatography and processed identically to the wild-type fusion protein. The samples analyzed before (1) and after (2) the refolding steps are shown in FIG. 5, panel III. The fusion protein containing a substitution mutation at the highly conserved Arg87->Lys in the protease protein did not show any processing, demonstrating that even a conservative mutation at this position totally inactivates the enzyme. These results are in agreement with earlier studies showing the synthesis, and expression of the exact coding region of the HIV-1 protease (99 amino acids) and another clone containing a substitution mutation, Arg87 to Lys (Louis et al., Biochem. Biophys. Res. Comm. 164:30–38 (1989) and Louis et al., Biochem. Biophys. Res. Comm. 159:87–94 (1989)). The mutant enzyme, as compared to the wild-type, was completely inactive as determined in assays employing synthetic peptides and a gag-related recombinant polyprotein as substrates (Louis et al., Biochem. Biophys. Res. Comm. 164:30–38 (1989) and Louis et al., Biochem. Biophys. Res. Comm. 159:87–94 (1989)). Inactivation of the enzyme is consistent with recent reports on the 3-D structure of HIV-1 protease, showing that the Arg87 ion pairs with the conserved Asp29 in forming the specific structure for the active site (Wlodawer et al., Science 245:616–21 (1989) and Lapatto et al., Nature 342:299–302 (1989)).

The full-length fusion protein from clone B-Mut87 after 5M urea denaturation and renaturation was separated from the other truncated products by size-exclusion column chromatography. The full-length fusion protein was incubated with 1/50 parts of the purified protease for 1 hr at 37° C., and the products of cleavage were analyzed by SDS-PAGE (FIG. 6). The fusion protein (600 ng) that was incubated for the same period of time in the absence of the wild-type protease showed the presence of the full-length product (lane 1) corresponding to a size of 53 kDa, and there were no detectable products of cleavage corresponding to the size of the maltose binding protein domain and the protease. Incubation of the fusion protein with the added purified wild-type protease (lane 2), resulted in the cleavage of the full-length fusion protein and the release of a product migrating to a position corresponding to the 38 kDa MBP (lane 2 & 3) and the 11 kDa protease (lane 2). The specificity of the released mutant protease form the fusion protein was confirmed by immunoblotting. This clearly shows that the unfused active protease is capable of cleaving the mutant protease from the fusion protein at both the N- and C-termini of the protease. These results are consistent with suggestions based on structural studies showing that the N- and C-terminal strands of the dimer protease are well organized (and away from the active site), and it is unlikely that the strands could be cleaved intramolecularly without disrupting the integrity of the dimer (Wlodawer et al., Science 245:616–21 (1989) and Lapatto et al., Nature 342:299–302 (1989)).

EXAMPLE 6

Analysis of Proteins

Gel electrophoresis using 10–20% gradient SDS-polyacrylamide gels or 10–20% Tricine-PAG was as specified in the figure legends. Appropriate amount of protein was mixed was 4x Laemmli sample buffer, heated to 90° C. for 4–5 min and used for electrophoresis. (Laemmli U. K., Nature 227:680–85 (1970)). Proteins were stained using Coomasie Brilliant Blue R-250 unless indicated otherwise. Immunoblotting was performing using antibody specific for the 99 amino-acid HIV-1 protease (Louis et al., Biochem. Biophys. Res. Comm. 164:30–38 (1989), Louis et al., Biochem. Biophys. Res. Comm. 159:87–94 (1989) and Copeland et al., Gene Anal. Tech. 5:109–15 (1988)).

EXAMPLE 7

Specific Proteolytic Activity of Fused and Unfused Protease

The fusion protein (1 µg) obtained from clone A (FIG. 3, lane 6) assayed for specific proteolytic activity using the synthetic nonpeptide substrate, showed an apparent specific activity of 40 pmoles/min/µg protein. The estimates of activity were calculated at 50% hydrolysis of the given substrate concentration. The purified fusion protein obtained from clone B before refolding showed a very low activity of approximately 5 pmoles/min/µg protein. The protease which was ≧98% pure after the cation-exchange column showed a specific activity of about 8500 pmoles/min/µg. The continuous spectrophotometric assay described previously for the retroviral proteased of HIV-1 an AMV wa used to measure the kinetic parameter $V_{max}/K_m$ for the purified HIV-1 protease (Nashed et al., Biochem. Biophys. Res. Comm. 163:1079–85 (1989)). Using peptide I as substrate, and assuming 100% active protein, $k_{cat}/K_m$ was estimated to be 48,000 $M^{-1}s$. at 37° C. (0.05 M MES at pH 6.0 2 M NaCl, 1 mM EDTA, 1 mM DTT and 5% glycerol).

EXAMPLE 8

Protease Assays

The enzymatic activity at various steps in the purification of the protease was monitored using the synthetic nonapeptide substrate Val-Ser-Gln-Asn-Tyr-Pro-Ile-Val-Gln, corresponding to the p24-p17 cleavage site in the natural gag precursor. Analysis of products of cleavage was by RP-HPLC (Louis et al., Biochem. Biophys. Res. Comm. 164:30–38 (1989), Louis et al., Biochem. Biophys. Res. Chem. 159:87–94 and Copeland et al., Gene Anal. Tech. 6:109–15 (1988)). The enzyme solution was assayed at 37° C. in a volume of 20 µl at a final concentration of 50 mM sodium phosphate (pH 6.5), 1.5 M NaCl, 1 mM DTT, 1 mM EDTA, 5% glycerol and 0.15 mM substrate. The continuous spectrophotometric assay was used to determine the pseudo-first-order rate constant $V_{max}/K_m$ (Nashed et al., Biochem. Biophys. Res. Comm. 163:1079–85 (1989)). In a typical measurement, 10 µl of 450 µM of peptide I (Ac-Lys-Ala-Ser-Gln-Asn-Phe (O₂)-Pro-Val-Val-NH₂) was added to 100 µl of 0.05 M MES at pH 6.0, 2.4 M NaCl, 1 mM EDTA, 1 mM DTT and 5% glycerol in a 100 µl microspectrophotometric cell at 37° C. The reaction was initiated by the addition of 10 µ of the enzyme (38.1 µg/ml) and monitored by following the decrease in absorption at 269 nm.

EXAMPLE 9

Overexpression of the Fused Protease Proteins

FIG. 3 shows the expression and partial purification of the fusion protein using clone A. This construct contains the entire coding region of the protease (see FIG. 2). Clone A was grown and induced. The cell pellet was lysed in Laemmli sample buffer, and the supernatant analyzed on 10% SDS-PAGE as shown in FIG. 3, lanes A (uninduced) and B (induced). As compared to the uninduced cell lysate the induced cells showed the distinct presence of a product of 49.5 kDa which agrees with the predicted size of the fusion of the maltose-binding protein domain-protease (compare with FIG. 2B). Densitometric analysis indicated the full-length fusion product was expressed to the extend of 3–4% of the total protein. However, when the soluble and the insoluble fractions obtained after lysis of the cells by sonication in buffer A were analyzed, about 90% of the total full-length fusion protein was present in the insoluble pellet (FIG. 3, lanes 1, 2 and 7). The insoluble pellet was washed 5–6 times in 25 mM sodium phosphate (pH 6.5), 0.2% Triton X-100 and 1 mM DTT to purify the inclusion bodies. Representative samples are shown in FIG. 3 (lanes 5 and 12). The majority of the proteins were removed in this step thereby enriching the amount of fusion protein in the preparation (compare lanes 2 and 5). To solubilize the fusion protein, the pellet obtained from the previous step (inclusion bodies) was treated with different concentrations of urea in buffer A, and the resulting pellets and supernatants were electrophoresed on 10–20% gradient (SDS-PAGE). The gels were either stained with Coomasie Blue or immunoblotted using antisera specific to the synthetic HIV-1 protease (Louis et al., *Biochem. Biophys. Res. Comm.* 164:30–38 (1989), Louis et al., 159:87–94 (1989) and Copeland et al., supra). At a concentration of 2 M urea, approximately 50% of the fusion protein was solubilized and recovered in the supernatant (FIG. 3, lanes 3, 8 and 9). The insoluble fusion protein was found to be entirely soluble in 5 M urea and all the fusion protein was recovered in the supernatant as shown in FIG. 3, lanes 4, 10 and 11.

Clone B which contains the sequences coding for 12 and 19 amino acids of the pol gene flanking the protease gene at the amino and the carboxyl termini, respectively, expressed a 53 kDa product. In contrast to clone A, the majority of the fusion protein was obtained in the soluble supernatant as shown in FIG. 4 (panel I, lane –(uninduced) and +(induced)). The plasmid construct in clone A is identical to clone B but for the absence of sequences coding for the pol region amino acids flanking the protease, suggestive of amino acids sequences that facilitate the solubility of the resultant fusion protein. The level of expression of the product was found to be the same as of clone A, the full-length product corresponding to abut 4% of the total protein. The specificity of the expressed product was analyzed by immunoblotting using HIV-1 protease antibody specifically and agrees with the predicted molecular mass of the fusion protein (FIG. 4, panel II, +lanes).

The tetrapeptide which is the recognition site of the factor 10a, protease was placed adjacent to the amino terminal Pro of the protease in clone A with the intention of purifying the 99 amino acid protease from the fusion protein. When using factor Xa protease to cleave the HIV protease (from clone A) or the Pol-Protease-Pol (from clone B) from the maltose binding protein domain, only limited and slow proteolysis was observed (<5% up to 48 hours at room temperature). It is possible that the factor 10a, protease site was not fully accessible for cleavage by this enzyme even after dissociating the aggregated fusion protein using urea.

Using clones A and B and the conditions of cell growth and lysis as described above processing of the protease from the full-length fusion protein *E. coli* was not observed (FIG. 4, panel II). An earlier report showed that a fusion protein of the Gag-Protease- Pol with LacZ was partially insoluble, formed inclusion bodies in *E. coli* and products of processed protease were observed (Giam et al., *J. Biol. Chem.* 262:14617–20 (1988)). Expression of the native sequence corresponding to bases 1672 (Nla4) to 1960 (Hae3) in clone BH5 (spans the protease gene) in *E. coli* showed processing the fusion protein to release the protease (Debouk et al., *Proc. Natl. Acad. Sci. USA* 84:8903–06 (1987)).

What is claimed is:

1. A method of producing a retroviral protease-resistant target protein comprising the steps of:

(i) (constructing) introducing an expression vector comprising a sequence encoding a fusion protein into a host cell; said fusion protein comprising;

(a) a retroviral protease-resistant binding domain;

(b) a retroviral protease which is downstream of said protease-resistant binding domain and is flanked on each side by at least four amino acids of pol sequence which is specifically recognized by said protease; and (c) the protease-resistant target protein where said target protein is downstream of the retroviral protease of step (b); and (ii) culturing said cell under conditions such that said fusion protein is produced.

2. The method of claim 1 further comprising the step of effecting proteolytic cleavage by said protease at said flanking sequences.

3. The method of claim 1 wherein the binding domain is selected from the B-galactosidase binding domain, the protein-A domain, the IgG-binding domain, the maltosc-binding domain and the glutathione-S-transferase binding domain.

* * * * *